United States Patent [19]

Grant, Jr.

[11] 4,115,459

[45] Sep. 19, 1978

[54] PREPARATION OF FLUOROTRINITROMETHANE

[75] Inventor: Louis R. Grant, Jr., Los Angeles, Calif.

[73] Assignee: The United States of America as represented by the Secretary of the Air Force, Washington, D.C.

[21] Appl. No.: 513,630

[22] Filed: Oct. 9, 1974

[51] Int. Cl.² ............................................. C07C 79/12
[52] U.S. Cl. ..................................................... 260/644
[58] Field of Search ......................................... 260/644

[56] References Cited

U.S. PATENT DOCUMENTS

| 3,127,736 | 4/1964 | Best et al. | 60/214 |
| 3,441,619 | 4/1969 | Gardner et al. | 260/644 |

*Primary Examiner*—Leland A. Sebastian
*Attorney, Agent, or Firm*—Joseph E. Rusz; Cedric H. Kuhn

[57] ABSTRACT

Fluorotrinitromethane is synthesized by reacting tetranitromethane with an adduct of an alkali metal fluoride and a fluorinated or chlorofluorinated acetone in an aprotic dipolar solvent.

7 Claims, No Drawings

PREPARATION OF FLUOROTRINITROMETHANE

RIGHTS OF THE GOVERNMENT

The invention described herein may be manufactured and used by or for the Government of the United States for all governmental purposes without the payment of any royalty.

FIELD OF THE INVENTION

This invention relates to a process for preparing fluorotrinitromethane.

BACKGROUND OF THE INVENTION

In U.S. Pat. No. 3,419,625, R. C. Doss discloses a method for preparing fluorotrinitromethane. As described in this patent, a solution is formed in a reaction zone by dissolving an alkali metal fluoride in a polar organic solvent. Tetranitromethane is then slowly added to the solution while maintaining the solution at a temperature in the range of zero to 100° C, preferably within the range of 0° to 30° C. After the addition of the tetranitromethane is completed, the reaction mixture is maintained within one of the aforementioned temperature ranges for a period of about 0.5 to 100 hours. It is stated that when the contacting temperature has been maintained within the preferred range of zero to 30° C, it is then usually desirable to substantially increase the temperature of the reaction mixture to a temperature of not more than 100° C for a short period of time. While the method described is suitable for preparing fluorotrinitromethane, it appears from the patent that it is only effective in producing the product in low yields. Thus, the maximum yield of fluorotrinitromethane obtained in the runs described in the examples was about 9 percent.

It is a principal object of this invention, therefore, to provide a process in which fluorotrinitromethane is produced in very high yields.

Other objects and advantages of the invention will become apparent to those skilled in the art upon consideration of the accompanying disclosure.

SUMMARY OF THE INVENTION

The present invention resides in the discovery of a process whereby fluorotrinitromethane can be prepared in very high yields. Broadly speaking, the process comprises the step of reacting tetranitromethane with an adduct of an alkali metal fluoride and a fluorinated or chlorofluorinated acetone in the presence of an aprotic solvent. When proceeding in accordance with the present process, it has been found that yields as high as 90 percent and higher can be obtained.

In carrying out the process of this invention, initially the adduct is formed by adding the alkali metal fluoride and the fluorinated or chlorofluorinated acetone to the aprotic solvent. After formation of the adduct, tetranitromethane is added to the solution. The reactions that occur in this two-step procedure are shown by the following equations:

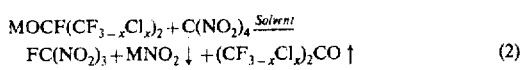

In the foregoing equations, M is an alkali metal such as potassium, cesium and rubidium and x is 0 to 2, inclusive. It is usually preferred to utilize potassium fluoride and hexafluoroacetone in forming the adduct. However, other fluorides, such as cesium and rubidium fluorides, and other acetones, such as pentafluorochloro-, tetrafluorodichloro-, trifluorotrichloro- and difluorotetrachloroacetones, can be employed. Use of the adduct allows the fluorination of tetranitromethane to occur in a homogeneous manner as represented by equation (2) above. In addition to the high product yields obtainable, a definite advantage associated with the homogeneous reaction is that only short reaction times are required.

Examples of aprotic dipolar solvents that can be employed include diglyme[bis(2-methoxyethyl)ether], N,N-dimethylformamide, acetonitrile, and the mono-, tri-, and tetraglymes. Diglyme is the preferred solvent because of the higher product yields obtained when it is used.

As previously mentioned, the adduct or complex is formed by adding an alkali metal fluoride and a fluorinated or chlorofluorinated acetone to an aprotic solvent. When forming the adduct, equimolar amounts of anhydrous fluoride and acetone are added to anhydrous solvent. In a preferred procedure for preparing the adduct, the acetone is bubbled into a suspension of alkali metal fluoride in the solvent, thereby providing a solution of the adduct. Formation of the adduct can be conveniently carried out at ambient temperature.

In the step wherein tetranitromethane is converted to fluorotrinitromethane [equation (2)], the alkali metal fluoride of the adduct functions as a fluorinating agent. The fluorinated or chlorofluorinated acetone that complexes with the fluoride acts as a catalyst in the fluorination of tetranitromethane. The mole ratio of adduct $[MOCF(C_{3-x}Cl_x)_2]$ to tetranitromethane $[C(NO_2)_4]$ generally falls in the range of 1:10 to 2.5 to 1. Molar concentrations usually range from 0.1 to 2.2 molar $MOCF(C_{3-x}Cl_x)_2$ and from 0.1 to 5 molar $C(NO_2)_4$. The reaction is carried out under anhydrous conditions at a temperature in the range of about −15° to 40° C. The reaction pressure usually ranges from 1 mm of mercury or less to 760 mm of mercury.

It is often preferred to employ an adduct of potassium fluoride and hexafluoroacetone $[KOCF(CF_3)_2]$ while conducting the reaction in diglyme. When utilizing these materials, it has been found that maximum yields and conversions can be obtained by employing certain specific reaction conditions. In this specific embodiment of the invention, about 2 moles of $KOCF(CF_3)_2$ per mole of $C(NO_2)_4$ and molar concentrations of about 2 for $KOCF(CF_3)_2$ and about 1 for $C(NO_2)_4$ are used. The reaction is conducted at 0° C under reduced pressure, e.g., at a pressure equal to or less than 1 mm of mercury.

As previously indicated, the homogeneous process of this invention requires only short reaction times. In general, the reaction times range from about 10 to 60 minutes. However, a period from 15 to 30 minutes is usually sufficient to obtain the high yields that are characteristic of the present process.

A more complete understanding of the invention can be obtained by referring to the following illustrative examples which are not intended, however, to be unduly limitative of the invention.

EXAMPLE I

A saturated solution of $KOCF(CF_3)_2$ (2.4 molar) was formed by bubbling $(CF_3)_2CO$ into a suspension of anhydrous KF in anhydrous diglyme. Thus, 15.6 g of anhydrous KF was suspended in 50 ml of anhydrous diglyme and 46.5 g of hexafluoroacetone was bubbled into the stirred suspension. The solution which was formed was analyzed and found to be 2.38 molar.

EXAMPLE II

A series of runs was carried out in which fluorotrinitromethane was prepared in accordance with the process of this invention. In each run, a known volume of saturated $KOCF(CF_3)_2$ solution in diglyme, prepared as described in Example I, was charged to a two-neck, round bottom flask under anhydrous conditions. The concentration of reactants in the runs was varied by varying the volume of diglyme used. The flask was connected via a trap, cooled with liquid nitrogen, to a vacuum pump. The reaction flask and its contents were cooled to 0° C at ambient pressure, and tetranitromethane was rapidly added. The reaction system was evacuated, and liberated $(CF_3)_2CO$, along with a small amount of the by-product NO, was collected in the −196° C cooled trap. The remaining solution, which contained the $FC(NO_2)_3$ and any unreacted $C(NO_2)_4$, was treated with twice its volume of water. This solution was extracted with diethyl ether, and the ethereal extract was dried over $MgSO_4$. The $FC(NO_2)_3$ product was isolated by fractional distillation of the dried ethereal extract. Identification of the $FC(NO_2)_3$ was made by comparing its infrared spectra and gas-liquid chromatographic retention time with authentic samples prepared by the elemental fluorination of $HC(NO_2)_3$.

Conditions at which the runs were conducted as well as results obtained are shown below in Table I.

TABLE I

| Run No. | Molar Concentration | | KF . HFA/TNM Mole Ratio | Time, hours | FTM[3] [4] Yield, % | TNM[5] Conversion, % |
|---|---|---|---|---|---|---|
| | TNM[1] | KF . HFA[2] | | | | |
| | 0.48 | 0.99 | 2.1 | 0.5 | 58 | 78 |
| 2 | 0.91 | 1.98 | 2.2 | 0.5 | 95 | 70 |
| 3 | 0.91 | 1.87 | 2.1 | 0.5 | 98 | 59 |
| 4 | 0.91 | 1.52 | 1.7 | 0.5 | 88 | 69 |
| 5 | 1.4 | 1.75 | 1.2 | 0.5 | 90 | 45 |

[1] TNM = tetranitromethane, $C(NO_2)_4$.
[2] KF . HFA = $KOCF(CF_3)_2$.
[3] FTM = fluorotrinitromethane, $FC(NO_2)_3$.
[4] Yield = $\frac{\text{mmoles of FTM}}{\text{mmoles of TNM Reacted}} \times 100$.
[5] Conversion = $\frac{\text{mmoles of TNM Reacted}}{\text{mmoles of TNM Charged}} \times 100$.

EXAMPLE III

Another series of runs was conducted at 0° C using diglyme as the solvent in the manner described in Example I except that the reactions were carried out at reduced pressures. Also, the reaction time for the runs was 60 minutes. Conditions at which the runs were conducted as well as results obtained are shown below in Table II.

TABLE II

| Run No. | Molar Concentration | | KF.HFA/TNM Mole Ratio | FTM Yield, % | TNM Conversion, % |
|---|---|---|---|---|---|
| | TNM | KF.HFA | | | |
| 6 | 0.91 | 1.83 | 2.0 | 91 | 90 |
| 7 | 1.16 | 2.07 | 1.8 | 89 | 80 |
| 8 | 1.33 | 2.00 | 1.5 | 87 | 83 |
| 9 | 1.84 | 1.88 | 1.0 | 86 | 77 |

As seen from the data in Tables I and II, the best FTM yields and TNM conversions were obtained at 0° C, using $KOCF(CF_3)_2$ to $C(NO_2)_4$ mole ratios of about 2 and $KOCF(CF_3)_2$ and $C(NO_2)_4$ molar concentrations of about 2 and 1, respectively. At lower mole ratios, whether the reactions were conducted at ambient or reduced pressures, the FTM yields remained high but the TNM conversions decreased. Similarly, at $KOCF(CF_3)_2$ to $C(NO_2)_4$ ratios of about 2 but at lower molar concentrations, the FTM yield decreased. However, in all runs the FTM yields were much greater than those disclosed in the prior art.

EXAMPLE IV

Runs were carried out under comparable conditions and in the manner described in Example II in order to compare the use of diglyme and N,N-dimethylformamide (DMF) as solvents. The reactions were conducted at ambient temperature and pressure. Conditions employed in the runs and results obtained are shown below in Table III.

TABLE III

| Run No. | Molar Concentration | | KF.HFA/TNM Mole Ratio | Solvent | Time, hours | FTM Yield, % | TNM Conversion, % |
|---|---|---|---|---|---|---|---|
| | TNM | KF.HFA | | | | | |
| 10 | 0.26 | 0.56 | 2.2 | Diglyme | 0.5 | 76 | 80 |
| 11 | 0.26 | 0.56 | 2.2 | DMF | 0.5 | 62 | 67 |
| | | | | | 1.0 | 32 | 73 |

As seen from the data in Table III, a lower yield of FTM was obtained in DMF than in diglyme under comparable conditions. Also, the greater solubility of $KNO_2$ in DMF caused more extensive side reactions with the FTM present as indicated by the change in FTM values after reaction times of 0.5 and 1.0 hour.

EXAMPLE V

A series of runs was conducted using diglyme as the solvent in the manner described in Example II. Conditions at which the runs were conducted and the results obtained are shown below in Table IV.

TABLE IV

| Run No. | Total Volume, Milliliters | Reaction Temperature, C | Reactants, moles TNM | Reactants, moles KF.HFA | KF.HFA/ TMM Ratio | Molar Concentration TNM | Molar Concentration KF.HFA | Time, hours | FTM Yield, % | TNM Conversion % |
|---|---|---|---|---|---|---|---|---|---|---|
| 12 | 20 | Ambient | 5.1 | 11.1 | 2.2 | 0.26 | 0.56 | 0.25 | 69 | 71 |
|  |  |  |  |  |  |  |  | 0.5 | 76 | 80 |
| 13 | 5.6 | Ambient | 5.1 | 11.1 | 2.2 | 0.91 | 1.98 | 0.25 | 55 | 80 |
|  |  |  |  |  |  |  |  | 0.5 | 70 | 85 |
| 14 | 5.6 | 0 | 5.1 | 11.1 | 2.2 | 0.91 | 1.98 | 0.25 | 96 | 70 |
|  |  |  |  |  |  |  |  | 0.5 | 95 | 70 |
| 15 | 5.6 | 0 | 5.1 | 10.5 | 2.1 | 0.91 | 1.87 | 0.25 | 95 | 55 |
|  |  |  |  |  |  |  |  | 0.5 | 98 | 59 |
| 16 | 5.6 | 0 | 5.1 | 8.5 | 1.7 | 0.91 | 1.52 | 0.25 | 86 | 69 |
|  |  |  |  |  |  |  |  | 0.5 | 88 | 69 |
| 17 | 6.0 | 0 | 8.4 | 10.5 | 1.2 | 1.4 | 1.75 | 0.25 | 88 | 40 |
|  |  |  |  |  |  |  |  | 0.5 | 90 | 45 |
| 18 | 10.6 | 0 | 5.1 | 10.5 | 2.1 | 0.48 | 0.99 | 0.25 | 60 | 80 |
|  |  |  |  |  |  |  |  | 0.5 | 58 | 78 |
| 19 | 5.6 | −15 | 5.1 | 12.0 | 2.4 | 0.91 | 2.14 | 0.25 | 97 | 55 |
|  |  |  |  |  |  |  |  | 1 | 92 | 63 |

As seen from the data in the foregoing table, the more dilute solutions gave lower FTM yields than the more concentrated ones. The optimum TNM and KF.HFA concentrations were 1 and 2 molar, respectively. The data also show that very high product yields are obtained in short reaction times.

As will be evident to those skilled in the art, modifications of the invention can be made in view of the foregoing disclosure without departing from the spirit and scope of the invention.

I claim:

1. A process for preparing fluorotrinitromethane which comprises reacting tetranitromethane with a complex having the following formula:

$$MOCF(CF_{3-x}Cl_x)_2,$$

wherein M is an alkali metal and $x$ is 0 to 2, inclusive, the reaction being conducted in an aprotic solvent.

2. The process according to claim 1 in which the reaction is carried out under anhydrous conditions for a period of about 10 to 60 minutes at a temperature in the range of about −15° to 40° C and at a pressure ranging from about 1 mm to 760 mm of mercury.

3. The process according to claim 2 in which the mole ratio of the complex to tetranitromethane is in the range of 1:10 to 2.5:1; the concentration of the complex ranges from about 0.1 to 2.2 molar; and the concentration of the tetranitromethane ranges from about 0.1 to 5 molar.

4. The process according to claim 3 in which the solvent is a member selected from the group consisting of monoglyme, diglyme, triglyme, tetraglyme, N,N-diethylformamide, and acetonitrile.

5. The process according to claim 1 in which M is potassium and $x$ is 0, and the solvent is diglyme.

6. The process according to claim 5 in which the reaction is carried out under anhydrous conditions for a period of about 15 to 30 minutes at 0° C and under reduced pressure.

7. The process according to claim 6 in which the mole ratio of the complex to tetranitromethane is about 2:1; the concentration of the complex is about 2 molar; and the concentration of the tetranitromethane is about 1 molar.

* * * * *